(12) United States Patent
Steffan et al.

(10) Patent No.: US 6,675,631 B1
(45) Date of Patent: Jan. 13, 2004

(54) METHOD FOR CONDUCTING CRASH TESTS USING A CARRIAGE AND CORRESPONDING DEVICE

(75) Inventors: Hermann Steffan, Linz (AT); Andreas Moser, Linz (AT); Manfred Hofinger, Linz (AT); Bertram Christian Geigl, Mattighofen (AT); Erich Mayrhofer, Linz (AT); Heinz Hoschopf, Jennersdorf (AT); Stefan Winkler, Graz (AT); Kurt Steiner, Graz (AT)

(73) Assignee: DSD Dr. Steffan Datentechnik Ges. m.b.H., Linz (AT)

( * ) Notice: Subject to any disclaimer, the term of this patent is extended or adjusted under 35 U.S.C. 154(b) by 0 days.

(21) Appl. No.: 10/018,298

(22) PCT Filed: May 9, 2000

(86) PCT No.: PCT/EP00/04139

§ 371 (c)(1),
(2), (4) Date: Jul. 30, 2002

(87) PCT Pub. No.: WO00/79236

PCT Pub. Date: Dec. 28, 2000

(51) Int. Cl.[7] ............................... G01N 3/22
(52) U.S. Cl. ............................... 73/12.04
(58) Field of Search .................. 73/12.04, 865.3, 73/865.4, 12.01, 11.04

(56) References Cited

U.S. PATENT DOCUMENTS

| | | | | |
|---|---|---|---|---|
| 5,483,845 A | * | 1/1996 | Stein et al. | 73/865.3 |
| 5,485,758 A | * | 1/1996 | Brown et al. | 73/865.8 |
| 5,652,375 A | * | 7/1997 | Da Re', Mario | 73/12.04 |
| 5,783,739 A | * | 7/1998 | Miller | 73/12.04 |
| 5,929,348 A | * | 7/1999 | Stein et al. | 73/865.3 |
| 6,035,728 A | * | 3/2000 | Jost | 73/865.3 |

FOREIGN PATENT DOCUMENTS

| | | | | |
|---|---|---|---|---|
| DE | 2 143 540 | 3/1973 | | G01M/7/00 |
| DE | 34 21 546 | 11/1985 | | G01M/7/00 |
| DE | 43 30 122 | 3/1994 | | G01M/7/08 |
| FR | 2 765 685 | 1/1999 | | G01M/17/00 |

OTHER PUBLICATIONS

U.S. Patent Publication U.S. 2002/0050179.*
U.S. Patent Publication U.S. 2002/0121144.*

* cited by examiner

Primary Examiner—Eric S. McCall
Assistant Examiner—Andre Allen
(74) Attorney, Agent, or Firm—Taylor & Aust, P.C.

(57) ABSTRACT

A method of conducting crash tests uses a crash-test carriage. The crash-test carriage is accelerated in accordance with a real deceleration curve to thereby simulate deceleration forces associated with a real collision, the crash-test carriage having a carriage drive apparatus associated therewith. The method includes the step of exerting an accelerating force on the crash-test carriage in an acceleration direction, the accelerating force exceeding a respective force required for acceleration in accordance with the real deceleration curve. The method also includes a step of exerting a braking force on the crash-test carriage in a direction opposite the acceleration direction in order to achieve a desired acceleration curve. The braking force is applied on one of the crash-test carriage and the carriage drive apparatus, the braking force being so large so as to accelerate the crash-test carriage in accordance with the desired acceleration curve.

21 Claims, 1 Drawing Sheet

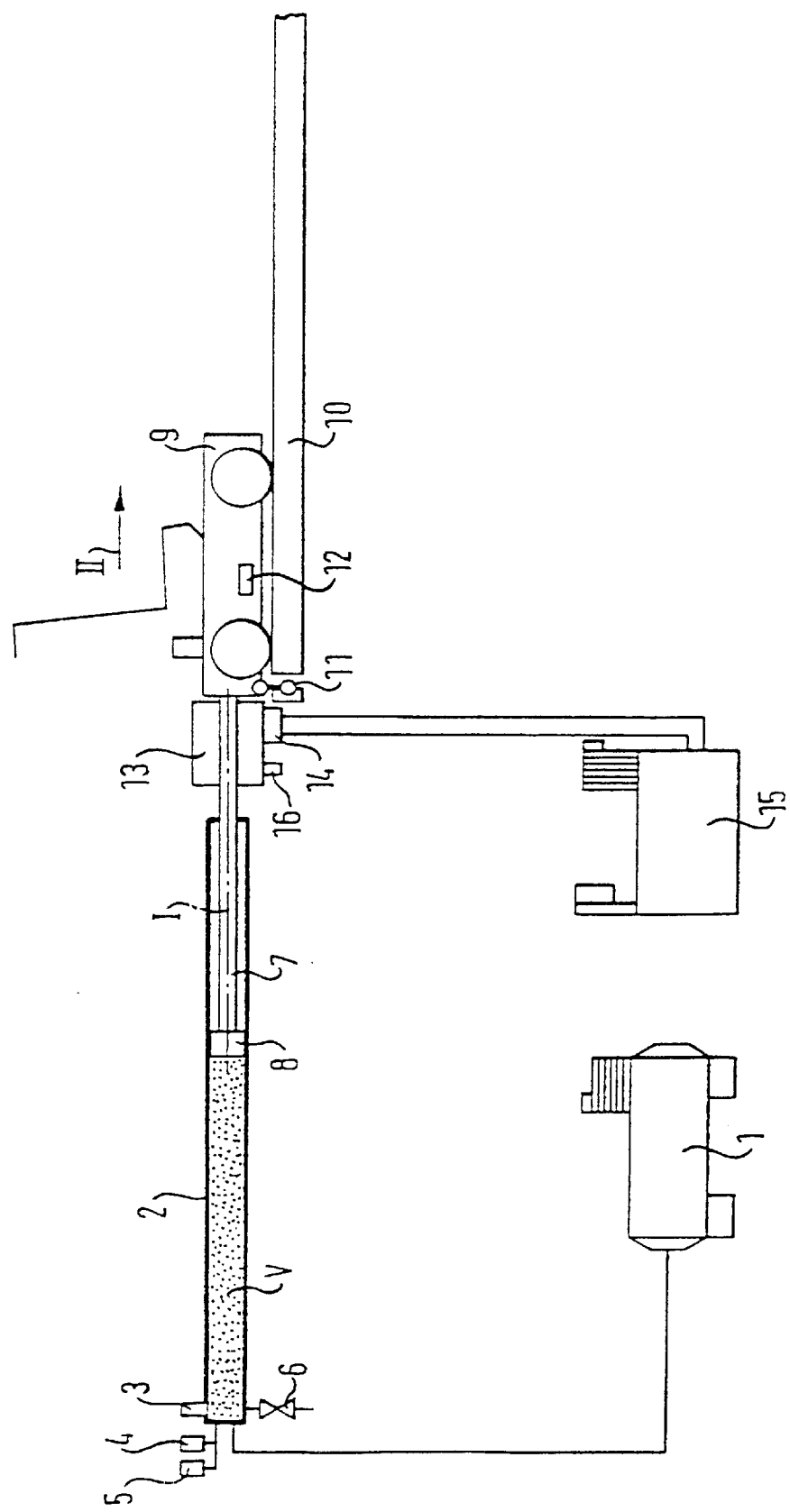

METHOD FOR CONDUCTING CRASH TESTS USING A CARRIAGE AND CORRESPONDING DEVICE

BACKGROUND OF THE INVENTION

1. Field of the Invention

The present invention relates to a method for conducting crash tests using a carriage, in particular for simulating the collision of a motor vehicle with an obstacle, in which the deceleration forces of a real collision are simulated. The invention moreover relates to an apparatus for carrying out such a method.

2. Description of the Related Art

When a vehicle collides with a resistance, for example another vehicle, in an accident, it is decelerated in accordance with the deformability of each of the vehicle and the resistance (e.g., the other vehicle). This deceleration initiates an acceleration onto the movable masses of the vehicle. In order to be able to investigate these acceleration forces, it is known to conduct real crash tests in which a vehicle is accelerated to a desired speed and collides with an obstacle. The vehicle is, however, destroyed thereby and cannot be used for further crash tests.

To allow acceleration forces to be investigated in accidents without having to destroy a whole vehicle for this purpose, so-called crash tests using a carriage are conducted, in which a carriage is accelerated to the desired speed, for example by a pre-stressed elastic cable. The carriage then collides with a deformable obstacle at this speed. However, with this kind of test, it is difficult to recreate deceleration curves from real crash tests.

It is therefore also known to simulate the deceleration of a real crash test by an acceleration of the test object. This means that the acceleration forces acting on the movable masses of the vehicle on collision with an obstacle are exerted directly via an acceleration of the crash-test carriage onto the test object. Real deceleration curves can thus be recreated substantially better.

In known methods, in order to conduct such tests, the carriage is accelerated by a thrust rod which is hydraulically moved out of a cylinder tube in accordance with a real deceleration curve. In order to recreate the real deceleration curve, the hydraulic pressure exerted on the thrust rod is controlled by a hydraulic valve. In view of the high degree of acceleration required, this thrust rod must be capable of being actuated at an extremely high rate and must be able to react very quickly. A plurality of calibration tests must be conducted for the adaptation to the real deceleration curve since such a valve cannot be regulated within the test time of a maximum of 100 milliseconds. This process is therefore relatively expensive and time-consuming.

SUMMARY OF THE INVENTION

The present invention provides a method for conducting crash tests using a carriage with which real deceleration curves can likewise be recreated very precisely, but which is less expensive and time-consuming, and includes an apparatus for carrying out such a method.

According to the present invention, during the test, a first force is exerted on the crash-test carriage in the direction of acceleration, this first force being larger than a respective second force required for acceleration in accordance with the real deceleration curve, on the one hand. In order to achieve the desired acceleration curve, a braking force opposite to the direction of acceleration is exerted on the crash-test carriage or on an apparatus driving it, this braking force being so large that the resulting force accelerates the carriage in accordance with the desired acceleration curve, on the other hand.

The generation of acceleration and the adaptation of the acceleration to a desired curve can be advantageously separated from one another by the exertion of an acceleration force on the crash-test slide, on the one hand, and of a braking force, on the other hand. The adaptation is thereby possible with a relatively low effort. In particular, a regulation can be carried out. Time-consuming calibration tests are thereby made superfluous so that the method overall requires much less effort than the one described with respect to the related art and, nevertheless, allows a very exact adaptation to the desired acceleration curve.

In accordance with an embodiment of the invention, the force acting in the direction of acceleration is produced pneumatically. It is possible to pneumatically generate a force in a simple manner and allows, likewise in a simple manner, a repeated conducting of crash tests using a carriage.

In accordance with a further embodiment of the invention, a pressure is generated in a pressure reservoir at a maximum braking force, the pressure corresponding at least to the maximum required acceleration force, and, subsequently, the brake is gradually opened in accordance with the acceleration curve. In this way, the adaptation of the acceleration to the acceleration curve can be achieved solely by a controlled or regulated opening of the brake. This adaptation is, in particular, of advantage when carrying out a real-time regulation.

In accordance with a further embodiment of the invention, the generation of the required pressure is controlled via a pressure sensor arranged in the pressure reservoir, in particular by using a computer. In this way, the exact pressure generation is ensured in the pressure reservoir.

In accordance with a further embodiment of the invention, the braking force is hydraulically transferred onto the brake carriage or onto an apparatus driving it. An exact control and regulation is thus possible in a particularly easy manner. As a result of the relatively low amount of hydraulic fluid required, valves with a comparatively low flow rate, in particular standard hydraulic valves, can be used, which can also be regulated in real time.

In accordance with a further embodiment of the invention, an emergency braking of an apparatus driving the crash-test carriage is carried out at the end of the crash test using a carriage, with the end of the crash test preferably being determined via the path covered, the time and/or the speed of the crash-test carriage. The exertion of an uncontrolled force on the crash-test carriage after the end of the test is thus prevented.

An apparatus for conducting the method includes, in accordance with the invention, a pressure chamber whose volume is restricted by a piston which acts on the crash-test carriage via a thrust rod; a compressor for generating the required pressure in the pressure chamber; and a braking device for acting on the crash-test carriage or on the thrust rod. Crash tests using a carriage in accordance with the invention can thus be conducted in an advantageous manner with pneumatic acceleration.

In accordance with a further embodiment of the invention, the pressure chamber has a safety valve to restrict the maximum pressure. Damage to the system due to excess pressure is thereby avoided.

In accordance with a further embodiment of the invention, a pressure sensor is present in the pressure chamber whose output signal is transmitted to a control unit to control the pressure generation. The achieving of the required pressure in the pressure chamber is thus ensured.

In accordance with a further embodiment of the invention, a pressure switch is provided in the pressure chamber whose response pressure lies somewhat below the safety valve pressure. Upon reaching the response pressure, the pressure switch switches off the compressor. The compressor is thus automatically switched off before the maximum permitted pressure is reached, and the occurrence of excess pressure is avoided.

In accordance with a further embodiment of the invention, the brake device acting on the crash-test carriage or on the thrust rod can be hydraulically actuated. This hydraulic actuation is advantageous for construction and allows a control, and in particular a regulation, of the braking force. A standard hydraulic valve is preferably provided for this purpose.

In accordance with a further embodiment of the invention, the braking force can be regulated dependent on the acceleration of the crash-test carriage. An acceleration sensor is provided therefor which measures the acceleration of the crash-test carriage. Another possibility includes regulating the braking force dependent on the desired pressure of the hydraulic brake.

In accordance with a further embodiment of the invention, the crash-test carriage can be displaced by a thrust rod, the thrust rod engaging loosely at the carriage, with the brake device preferably acting on the thrust rod. This set-up is advantageous for construction and also allows the crash-test carriage to roll out at the end of the test.

In accordance with a further embodiment of the invention, a plurality of units are provided in order to generate the acceleration force. The force required to accelerate the crash-test carriage can thereby be generated more simply.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawing, wherein:

FIG. 1 is a side view of a crash-test carriage system of the invention.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the sole drawing, FIG. 1, a compressor 1 generates, in a compressed air tube 2, an air pressure required for conducting a crash test using a carriage. A safety valve 3 ensures that a maximum pressure is not exceeded in compressed air tube 2.

A pressure sensor 4 is connected to compressed air tube 2 and measures the actual pressure in compressed air tube 2. This measurement is forwarded to a control computer (not shown here). When the desired pressure is reached, the control computer initiates the switching off of compressor 1. In addition, a pressure switch 5 can be connected to compressed air tube 2, the response pressure of pressure switch 5 lying somewhat below the response pressure of safety valve 3. When pressure switch 5 responds, compressor 1 is switched off. Finally, a rotary valve 6 is connected to compressed air tube 2, and the pressure in compressed air tube 2 can be lowered to ambient pressure thereby.

A thrust rod 7 is inserted into compressed air tube 2 and has a piston 8 at its inner end which is sealingly guided in compressed air tube 2 and thereby limits compressed air volume V in compressed air tube 2. The other end of thrust rod 7 loosely engages at a crash-test carriage 9. Crash-test carriage 9 can be displaced on rails 10 in the direction of longitudinal axis I of thrust rod 7. The starting position of crash-test carriage 9 is determined by a stop 11. Furthermore, an acceleration sensor 12 is provided on crash-test carriage 9, and the acceleration of crash-test carriage 9 in the direction of arrow II can be measured thereby and transmitted to the control computer.

A hydraulically actuable brake device 13 engages at thrust rod 7. The flow of hydraulic fluid 15 from a hydraulic unit 15 to brake device 13 is regulated via a servo valve 14. Moreover, a pressure sensor 16 is present at brake device 13. Pressure sensor 16 measures the brake pressure and transmits a related signal to the control device/computer.

To conduct a crash test using a carriage, servo valve 14 is first fully opened so that brake device 13 is closed, and thrust rod 7 is held at its starting position at which crash-test carriage 9 contacts stop 11. Now, the required pressure is built up in compressed air tube 2 via compressor 1. When the test starts, servo valve 14 begins to regulate the braking force on thrust rod 7 in accordance with a desired acceleration curve. The actual acceleration of crash-test carriage 9 is measured directly via acceleration sensor 12 and is used in the control computer to regulate the braking force. Alternatively, the braking force can be measured via brake pressure sensor 16, and the braking force can be regulated dependent on the brake pressure.

As soon as at least one of the termination criteria, path covered, time and/or speed of crash-test carriage 9, has been satisfied, servo valve 14 opens fully again so that an emergency braking of thrust rod 7 is initiated. Crash-test carriage 9 thereby lifts off of thrust rod 7 and rolls out on rails 10. For the next test, carriage 9 and thrust rod 7 are pushed back into the starting position at which carriage 9 contacts stop 11.

The conducting of the crash test using a carriage 9 can be carried out in a particularly suitable manner with this arrangement, with a very precise adaptation to a real acceleration curve being achieved by the separation of the generation of the acceleration force and the adaptation of the acceleration to a desired acceleration curve via brake device 13. The pneumatic generation of the acceleration force and the use of hydraulic brake device 13 are in this respect advantageous, in particular, for a repeated conducting of the crash test using carriage 9.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Reference Numeral List 1 compressor
2 compressed air tube
3 safety valve
4 pressure sensor 5 pressure switch
6 rotary valve
7 thrust rod
8 piston
9 crash-test carriage
10 rails
11 stop
12 acceleration sensor
13 brake device
14 servo valve
15 hydraulic unit
16 brake pressure sensor
I longitudinal axis of 7
II direction of acceleration
V compressed air volume

What is claimed is:

1. A method of conducting crash tests using a crash-test carriage, said crash-test carriage being accelerated in accordance with a real deceleration curve to thereby simulate deceleration forces associated with a real collision, said crash-test carriage having a carriage drive apparatus associated therewith, the method comprising the steps of:

exerting an accelerating force on said crash-test carriage in an acceleration direction, said accelerating force exceeding a respective force required for acceleration in accordance with the real deceleration curve; and exerting a braking force on said crash-test carriage in a direction opposite said acceleration direction in order to achieve a desired acceleration curve, said braking force being applied on one of said crash-test carriage and said carriage drive apparatus, said braking force controlled so as to accelerate said crash-test carriage in accordance with the desired acceleration curve.

2. The method of claim 1, wherein a collision of a motor vehicle with an obstacle is simulated.

3. The method of claim 1, wherein said braking force is regulated in a manner dependent upon the real acceleration of said crash-test carriage.

4. The method of claim 1, wherein said accelerating force is generated pneumatically.

5. The method of claim 4, wherein said crash-test carriage has a pressure-generating source associated therewith, said pressure-generating source comprising a pressure chamber, the method further including the steps of:

generating in the pressure chamber, at a maximum braking force, a pressure that corresponds at least to a maximum required acceleration force; and subsequently gradually reducing said braking force in accordance with the desired acceleration curve.

6. The method of claim 5, wherein said pressure chamber has a pressure sensor associated therewith for measuring the pressure therein, said generating of said pressure being controlled via said pressure sensor.

7. The method of claim 5, further including the step of lowering the pressure in said chamber to ambient pressure at an end of said crash test.

8. The method of claim 1, wherein said braking force is hydraulically transmitted to one of said crash-test carriage and said carriage drive apparatus.

9. The method of claim 1, further including the step of emergency braking of said carriage drive apparatus at an end of said crash test.

10. The method of claim 9, wherein said end of said crash test is determined based upon at least one of a path covered by said crash-test carriage, a length of time associated with said crash test and a speed of said crash-test carriage.

11. An apparatus for conducting crash tests using a crash-test carriage, said crash-test carriage being accelerated in accordance with a real deceleration curve to thereby simulate deceleration forces associated with a real collision, said crash-test carriage having a carriage drive apparatus associated therewith, the apparatus comprising:

a pressure-generating source having a pressure chamber associated therewith, said pressure chamber having a chamber volume;

a piston located within said pressure-generating source, said piston restricting said chamber volume;

a thrust rod positioned within said pressure-generating source opposite said chamber volume, said thrust rod being operatively coupled with said piston, said thrust rod being configured for acting upon said crash-test carriage;

a compressor connected to said pressure chamber, said compressor generating a required pressure in said pressure chamber; and a brake device in controlling connection with one of said crash-test carriage and said thrust rod, thereby controlling the acceleration force such that said crash-test carriage accelerates in accordance with a desired acceleration curve.

12. The apparatus of claim 11, further including a safety valve operatively connected with said pressure chamber, said safety valve restricting a maximum pressure within said pressure chamber.

13. The apparatus of claim 11, further including a pressure sensor operatively connected to said pressure chamber, said pressure sensor producing an output pressure signal, said output pressure signal being used to control pressure generation within said pressure chamber.

14. The apparatus of claim 12, further including a pressure switch operatively connected with said pressure chamber, said pressure switch having a switch response pressure associated therewith, said safety valve having an associated valve response pressure, said switch response pressure being less than said valve response pressure, said pressure switch being operatively coupled with said compressor, said pressure switch being configured for switching off said compressor when said pressure within said pressure chamber is equal to at least said switch response pressure.

15. The apparatus of claim 11, further including a hydraulic unit coupled with said brake device, said brake device being hydraulically actuated by said hydraulic unit.

16. The apparatus of claim 15, further including a hydraulic valve associated with said brake device and said hydraulic unit, said hydraulic valve being configured for regulating a braking force generated by said brake device.

17. The apparatus of claim 1, wherein said braking device generates a braking force, said braking force being regulated in a manner dependent upon an acceleration of said crash-test carriage.

18. The apparatus of claim 1, wherein said braking device generates a braking force, said braking force being regulated in a manner dependent upon a desired brake pressure of said brake device.

19. The apparatus of claim 1, wherein said thrust rod loosely engages said crash-test carriage, said thrust rod thereby being configured for displacing said crash-test carriage.

20. The apparatus of claim 1, wherein said brake device configured for acting upon said thrust rod.

21. The apparatus of claim 1, wherein one said compressor and a corresponding said pressure chamber together comprise an acceleration unit, at least one said acceleration unit being provided for generating a required acceleration force.

* * * * *

(12) EX PARTE REEXAMINATION CERTIFICATE (6882nd)
United States Patent
Steffan et al.

(10) Number: US 6,675,631 C1
(45) Certificate Issued: Jun. 16, 2009

(54) METHOD FOR CONDUCTING CRASH TESTS USING A CARRIAGE AND CORRESPONDING DEVICE

(75) Inventors: Hermann Steffan, Linz (AT); Andreas Moser, Linz (AT); Manfred Hofinger, Linz (AT); Bertram Christian Geigl, Mattighofen (AT); Erich Mayrhofer, Linz (AT); Heinz Hoschopf, Jennersdorf (AT); Stefan Winkler, Graz (AT); Kurt Steiner, Graz (AT)

(73) Assignee: Illinois Tool Works Inc. (ITW), Glenview, IL (US)

Reexamination Request:
No. 90/008,950, Dec. 5, 2007

Reexamination Certificate for:
Patent No.: 6,675,631
Issued: Jan. 13, 2004
Appl. No.: 10/018,298
Filed: Jul. 30, 2002

(22) PCT Filed: May 9, 2000
(86) PCT No.: PCT/EP00/04139
§ 371 (c)(1),
(2), (4) Date: Jul. 30, 2002
(87) PCT Pub. No.: WO00/79236
PCT Pub. Date: Dec. 28, 2000

(51) Int. Cl.
*G01N 3/22* (2006.01)
*G01N 3/00* (2006.01)

(52) U.S. Cl. .................................................. 73/12.04
(58) Field of Classification Search ................... None
See application file for complete search history.

(56) References Cited
PUBLICATIONS

Hofinger Entwicklung einer acktiven Crash–Schlitten–Anlag.

*Primary Examiner*—My-Trang Ton

(57) ABSTRACT

A method of conducting crash tests uses a crash-test carriage. The crash-test carriage is accelerated in accordance with a real deceleration curve to thereby simulate decelaration forces associated with a real collision, the crash-test carriage having a carriage drive apparatus associated therewith. The method includes the step of exerting an accelerating force on the crash-test carriage in an acceleration direction, the accelerating force exceeding a respective force required for acceleration in accordance with the real deceleration curve. The method also includes a step of exerting a braking force on the crash-test carriage in a direction opposite the acceleration direction in order to achieve a desired acceleration curve. The braking force is applied on one of the crash-test carriage and the carriage drive apparatus, the braking force being so large so as to accelerate the crash-test carriage in accordance with the desired acceleration curve.

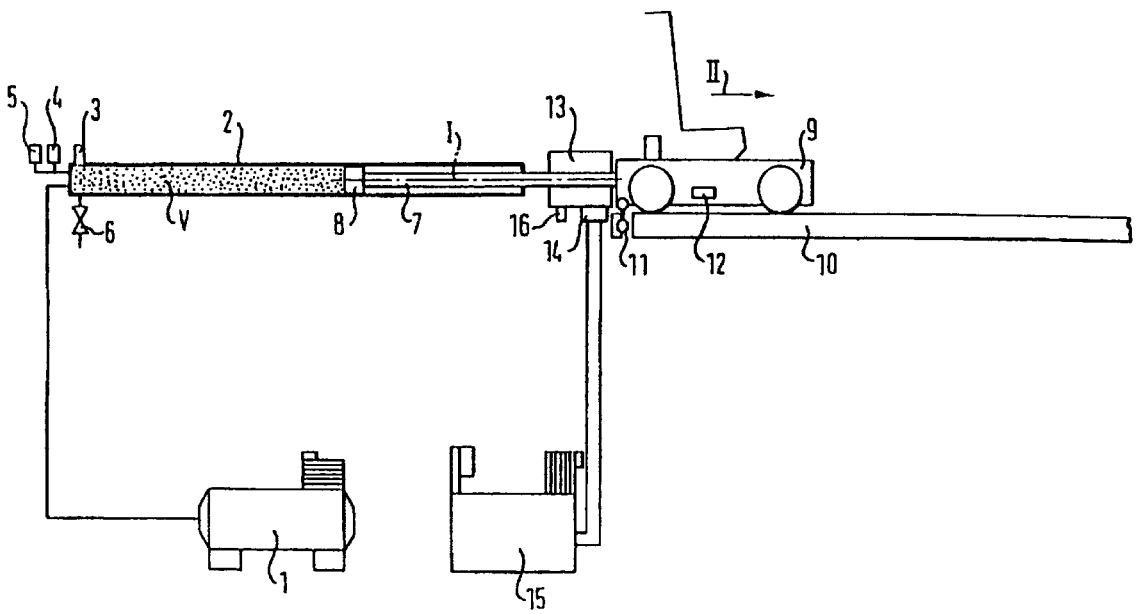

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3, 17 and 18 are cancelled.

Claims 1, 11 and 20 are determined to be patentable as amended.

Claims 2, 4–10, 12–16, 19 and 21, dependent on an amended claim, are determined to be patentable.

1. A method of conducting crash tests using a crash-test carriage, said crash-test carriage being accelerated in accordance with a real deceleration curve to thereby simulate deceleration forces associated with a real collision, said crash-test carriage having a carriage drive apparatus associated therewith, the method comprising the steps of:
   exerting an accelerating force on said crash-test carriage in an acceleration direction, said accelerating force exceeding a respective force required for acceleration in accordance with the real deceleration curve; and
   exerting a braking force on said crash-test carriage, *by way of a braking device*, in a direction opposite said acceleration direction in order to achieve a desired acceleration curve, said braking force being applied on one of said crash-test carriage and said carriage drive apparatus, said braking force controlled *in a manner dependent upon a desired brake pressure of said braking device as an alternative to a measured acceleration of said crash-test carriage* so as to accelerate said crash-test carriage in accordance with the desired acceleration curve.

11. An apparatus for conducting crash tests using a crash-test carriage, said crash-test carriage being accelerated in accordance with a real deceleration curve to thereby simulate deceleration forces associated with a real collision, said crash-test carriage having a carriage drive apparatus associated therewith, the apparatus comprising:
   a pressure-generating source having a pressure chamber associated therewith, said pressure chamber having a chamber volume;
   a piston located within said pressure-generating source, said piston restricting said chamber volume;
   a thrust rod positioned within said pressure-generating source opposite said chamber volume, said thrust rod being operatively coupled with said piston, said thrust rod being configured for acting upon said crash-test carriage;
   a compressor connected to said pressure chamber, said compressor generating a required pressure in said pressure chamber; and
   a brake device in controlling connection with one of said crash-test carriage and said thrust rod, thereby controlling the acceleration force *by exerting a braking force controlled in a manner dependent upon a desired brake pressure of said brake device as an alternative to a measured acceleration of said crash-test carriage* such that said crash-test carriage accelerates in accordance with a desired acceleration curve.

20. The apparatus of claim 1, wherein said brake device *is* configured for acting upon said thrust rod.

* * * * *